United States Patent [19]

Wakai et al.

[11] Patent Number: 5,123,844

[45] Date of Patent: Jun. 23, 1992

[54] LIVING HARD TISSUE REPLACEMENT PREPARED BY SUPERPLASTIC FORMING OF A CALCIUM PHOSPHATE BASE

[75] Inventors: Fumihiro Wakai; Yasuharu Kodama, both of Nagoya; Tohru Nonami, Ichikawa; Nobuo Yasui, Narita, all of Japan

[73] Assignees: Agency of Industrial Science and Technology, Ministry of International Trade and Industry; TDK Corporation, Tokyo, Japan

[21] Appl. No.: 540,926

[22] Filed: Jun. 20, 1990

[30] Foreign Application Priority Data

Jun. 20, 1989 [JP] Japan .................. 1-155758
Jun. 20, 1989 [JP] Japan .................. 1-157514
Jun. 5, 1990 [JP] Japan .................. 2-146711

[51] Int. Cl.⁵ .......................................... A61C 8/00
[52] U.S. Cl. ................................. 433/201.1; 433/173; 623/16
[58] Field of Search ............... 433/173, 201.1; 623/16; 128/60

[56] References Cited

U.S. PATENT DOCUMENTS 4,429,691  2/1984  Niwa et al. ........................ 606/77
4,599,085  7/1986  Riess et al. ........................ 433/201.1

*Primary Examiner*—John J. Wilson
*Attorney, Agent, or Firm*—Oblon, Spivak, McClelland, Maier & Neustadt

[57] ABSTRACT

A living hard tissue replacement is prepared by subjecting a calcium phosphate base ceramic material to superplastic forming. Also provided is a method for preparing a composite body comprising the step of joining a cover of a calcium phosphate base ceramic material to a substrate of a heterogeneous material by superplastic forming. Superplastic forming is often performed by hot isostatic pressing. The living hard tissue replacement and composite body are useful as artificial dental roots, dental crowns, and bones.

14 Claims, 3 Drawing Sheets

LIVING HARD TISSUE REPLACEMENT PREPARED BY SUPERPLASTIC FORMING OF A CALCIUM PHOSPHATE BASE

This invention relates to living hard tissue replacements obtained by shaping a calcium phosphate base ceramic material having biological activity by superplastic forming, and a method for preparing the same. It also relates to a method for preparing a composite body by joining a calcium phosphate base ceramic material to a material of different type through superplastic forming.

BACKGROUND OF THE INVENTION

A variety of filling and repairing materials have been utilized to restore the function and configuration of a deficient part of a living body. Typical filling and repairing materials for living bodies include artificial bones and analogues such as artificial dental roots and crowns as well as artificial joints. They are generally known as living hard tissue replacements.

These living hard tissue replacements are required to be mechanically strong, tough, and stable in living bodies and should have high affinity to living bodies. Another important factor is ease of shaping because a living hard tissue replacement has to be a custom-made part conforming to an individual patient's deficient site.

The biological affinity used in this context means how a living hard tissue replacement adapts itself to and merges or assimilates with the surrounding living tissue where the replacement is embedded or implanted. Thus, a material having high biological affinity is scarcely recognized as xenobiotic by the surrounding tissue. Particularly when such material is used as an artificial bone, it can promote osteogenesis from the surrounding bone to eventually form a firm bond between itself and the bone tissue.

Among the currently available artificial bone materials, those featuring high mechanical strength and in vivo stability are metals such as titanium and zirconium, alloys containing such metals, and ceramics such as alumina, silicon nitride, and zirconia. The materials having high mechanical strength and in vivo stability, however, have low biological affinity, that is, are unlikely to assimilate with living tissue, resulting in an extended cure time and poor adherence to the living tissue. In addition, they must be extracted and removed by surgical operations after they have performed their duties.

Typical of known materials having high biological affinity are calcium phosphate base ceramic materials including apatite, especially hydroxyapatite and tricalcium phosphate. Apatite has the best biological affinity as understood from the fact that bone is essentially composed of apatite if organic components are excluded.

As previously described, most living hard tissue replacements have a particular shape and a complex profile depending on individual patients. In particular, oral surgical implants such as dental roots and crowns widely vary in shape depending on individual patients and sites. In the prior art, an implant of desired shape is generally prepared from calcium phosphate base ceramic material, typically apatite by molding the material by an injection molding or casting technique, followed by sintering and reshaping. These manufacturing methods, however, have many drawbacks including lack of dimensional precision, difficulty to change the shape, surface defects induced by reshaping, and losses of strength due to stresses.

Further, it is critical for implants to adhere to living bones. For promoted adherence, it is important to control the surface nature of implants. However, ordinary processing techniques have limited freedom to control the surface nature, for example, to achieve a mirror finish or a rough surface.

SUMMARY OF THE INVENTION

A primary object of the present invention is to eliminate the drawbacks of prior art living hard tissue replacements and to provide a novel and improved living hard tissue replacement which can be readily formed to the desired shape, surface nature, and dimensions in conformity to an individual patient.

Another object of the present invention is to provide a method for preparing such a living hard tissue replacement.

A further object of the present invention is to provide a method for preparing a composite body having increased mechanical strength which is applicable as a living hard tissue replacement.

The inventors have found that calcium phosphate base ceramic materials show superplastic nature. The present invention is predicated on this finding.

The superplasticity of ceramics is the nature that ceramics show extremely high ductility under low stresses at a temperature substantially lower, e.g., by 500° C., than the sintering or forging temperature as described in the literature, for example, Journal of the JSTP, 29, 326 (Mar. 1988); Ceramics, 24, 2 (1989); and Tetsu to Hagane (Iron and Steel), 75, 3 (1989). Typical prior art ceramic materials known to show superplastic nature are Y-TZP (yttria-stabilized tetragonal $ZrO_2$ polycrystals) and $ZrO_2$—$Al_2O_3$ systems. To take advantage of plastic deformation, extrusion molding and thin plate molding have been attempted on them. Attempts have also been made to diffusion bond two pieces of the same material by superplastic forming.

Nevertheless, it has never been reported that calcium phosphate base ceramic materials including apatite and tricalcium phosphate show superplastic nature. We have first discovered that calcium phosphate base ceramic materials show superplastic nature.

According to a first aspect of the present invention, there is provided a living hard tissue replacement obtained by the superplastic forming of a calcium phosphate base ceramic material.

According to a second aspect of the present invention, there is provided a method for preparing a living hard tissue replacement comprising the step of superplastic forming a calcium phosphate base ceramic material. Preferably, the ceramic material has an average grain size of up to 10 $\mu$m, and the superplastic forming is carried out at a temperature of 500° to 1,600° C.

According to a third aspect of the present invention, there is provided a method for preparing a composite body comprising the step of joining a calcium phosphate base ceramic material and a material of different type by superplastic forming.

BRIEF DESCRIPTION OF THE DRAWINGS

The above and other objects, features, and advantages of the present invention will be better understood from the following description taken in conjunction with the accompanying drawings, in which.

DESCRIPTION OF THE PREFERRED EMBODIMENTS

Figure 1:
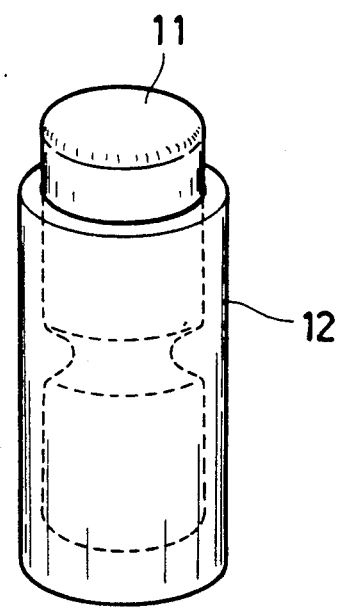
FIGS. 1 to 3 are perspective views illustrating steps of the method for preparing a composite body as a living hard tissue replacement according to the invention.

The ceramic materials used in the practice of the present invention include a variety of ceramic materials based on calcium phosphate although apatite and tricalcium phosphate are often used. Preferred are apatite series calcium phosphates having a stoichiometric composition: $Ca_{10}(PO_4)_6X_2$ wherein X is a hydroxyl group or a halogen atom (e.g., fluoro and chloro). The most preferred calcium phosphate materials are hydroxyapatite and fluoroapatite, typically having an atomic calcium to phosphorus (Ca/P) ratio of from 160/100 to 175/100. Also useful is tricalcium phosphate $Ca_3(PO_4)_2$.

In the practice of the present invention, these calcium phosphate base ceramic materials are used in sintered form. The sintered body may contain sintering aids such as $Al_2O_3$, $SiO_2$, MgO and CaO in an amount of up to 5% by weight of the body.

The calcium phosphate base ceramic materials in sintered form preferably have an average grain size of up to 10 μm. It is to be noted that the average grain size may be measured by means of a scanning electron microscope (SEM) by determining an average grain area, and determining the average diameter of a phantom circle having the average grain area. The average diameter is the average grain size. Less superplasticity is exerted with an average grain size in excess of 10 μm. Better results are obtained from ceramic materials having an average grain size of up to 2 μm, more preferably up to 1 μm, most preferably up to 0.7 μm, while the minimum grain size is usually of the order of 0.005 μm.

Since the sintered body approximately maintains its average grain size during superplastic forming to be described later, the average grain size of the sintered body after superplastic forming is somewhat or little changed from that before superplastic forming. It should be understood that if the sintered body is subjected to superplastic forming while compressing under a unidirectional stress, the grains are generally recognized to undergo distortion and orientation.

The shape and dimensions of the sintered body are not critical since they may be determined for a particular purpose. The average grain size of the sintered body is generally of the order of 10 to 100% of that of the finally formed article.

The stock materials from which sintered bodies are formed are preferably apatite and tricalcium phosphate as previously defined. The stock materials may be either biotic apatites collected from bones and teeth of various vertebrate animals or synthetic apatites prepared by dry and wet processes. Powder stock material of calcium phosphate base ceramic material such as apatite and tricalcium phosphate is sintered to form a sintered body having superplasticity. The powder stock material preferably has a surface area of about 1 to about 100 m²/g as measured by the BET method. The stock material may be blended with sintering aids as previously described.

The powder stock material is then shaped. For shaping, the material is subjected to unidirectional pressing under a pressure of about 1 to about 3,000 kg/cm² and then to cold isostatic pressing (CIP) under a pressure of about 1,000 to about 10,000 kg/cm².

The shaped material is usually sintered at a temperature of 500° to 1,600° C., especially 700° to 1,200° C. for about 3 minutes to about 30 hours. During sintering, concurrent hot pressing or hot isostatic pressing (HIP) is preferably carried out for densification purposes. These pressing techniques favor a pressure of 50 to 5,000 atmospheres. The atmosphere may be an inert gas, air, hydrogen or vacuum.

The material may be calcined at about 700° to about 1,350° C. for about 3 minutes to about 30 hours before sintering.

In this way, there is obtained a sintered body with the above-described average grain size, preferably having a relative density of at least 70%, more preferably at least 90%, and most preferably at least 99.5%.

The next step is to process the sintered material by superplastic forming. The forming temperature ranges from 500° C. to a temperature lower than the sintering temperature, preferably lower by 50° C. More illustratively, the temperature ranges from 600° to 1,300° C., especially from 800° to 1,200° C. The superplastic forming in the first form of the invention uses a mold with a cavity having the shape and dimensions corresponding to the intended implant and is performed by subjecting the sintered calcium phosphate base Q ceramic material to extrusion shaping or embossing. During the process, both the sintered material and the mold should be heated to a temperature at which the sintered material exhibits superplasticity. The sintered calcium phosphate base ceramic material subject to superplastic forming is preferably in the form of thin plates or sheets, granules, and powder particles. Superplastic forming causes thin sheets or granules to fuse together to form a continuous crystalline structure at their interface, resulting in a very firm junction.

The compression rate, compression force, and deformation during superplastic forming vary with a particular technique employed. Preferred forming parameters include a compression rate of 0.01 to 50 mm/min., a compression force of 1 to 2,000 MPa, more preferably 1 to 500 MPa, especially 1 to 100 MPa, and a deformation of about 0.1 to about 1.5 in true strain.

In the case of embossing, the sintered calcium phosphate base ceramic material which has been shaped to approximately the desired shape, for example, the dental crown shape may be used. In this case, the deformation to be achieved by superplastic forming or embossing is minimized, with the benefit of ease of forming.

The superplastic forming may also be carried out by a hot pressing technique using a mold or a hot isostatic pressing (HIP) technique. Further, the superplastic forming may be repeated any times if desired.

In general, the thus formed calcium phosphate base ceramic material has experienced a change in grain size as low as 100% or less. It is sometimes observed that the grains have undergone slippage along the grain boundary, deformation, and orientation.

In the second form of the present invention, a sintered calcium phosphate base ceramic material as previously described and a material of different type, that is, other than the calcium phosphate base ceramic material are placed one on another to form a stack and joined together by superplastic forming. More particularly, the two materials are placed in pressure contact at a predetermined temperature to provide a diffusion or solid phase bond.

The temperature, compression rate, compression force, deformation, and other parameters for joint formation are substantially the same as previously described for the superplastic forming.

Pressure contact may be achieved between a calcium phosphate base ceramic material and a substrate of a different material by pressing the stacked materials in close contact using a press or punch or by extruding or reverse extruding the calcium phosphate base ceramic material through a die using a punch formed of the substrate material. Pressure contact may also be accomplished by rolling and drawing combined with extrusion.

The superplastic forming may be repeated any time if desired.

The superplastic forming joins the sintered calcium phosphate base ceramic material and the heterogeneous material together into a composite body having a bond strength as high as 30 to 1,000 MPa, especially 100 to 1,000 MPa although the bond strength depends on the type of the heterogeneous material.

The calcium phosphate base ceramic material in the composite body sometimes experiences a change in grain size as previously described.

The material of different type to be joined is not particularly limited as long as it is different from the calcium phosphate base ceramic material. It may be selected from various ceramic materials, various metals, various glasses, composites thereof, and other suitable materials. The material to be joined may or may not exhibit plastic deformation during pressure joining. Also, it may or may not exhibit superplastic deformation. If the material to be joined has superplastic nature, then it is possible to join more than two materials together at the same time. Most often, the material to be joined has high mechanical strength and functions as a substrate or support.

In the preferred embodiment of the second form wherein the calcium phosphate base ceramic material covers a substrate of different material, two materials are held in close contact at a predetermined temperature and pressure by hot isostatic pressing (HIP), thereby achieving a diffusion or solid phase bond therebetween. The superplastic ceramic material such as calcium phosphate material as the cover layer undergoes superplastic deformation during the HIP process.

For the HIP process, the temperature generally ranges from 500° C. to lower than the sintering temperature, usually from 500° C. to 1,600° C. The compression force generally ranges from 1 to 2,000 MPa, usually from 1 to 500 MPa. The heating/pressing time may vary over a wide range of from about 6 seconds to 1,500 minutes. The deformation ranges from about 0.1 to about 1.5 in true strain.

Figure 2:
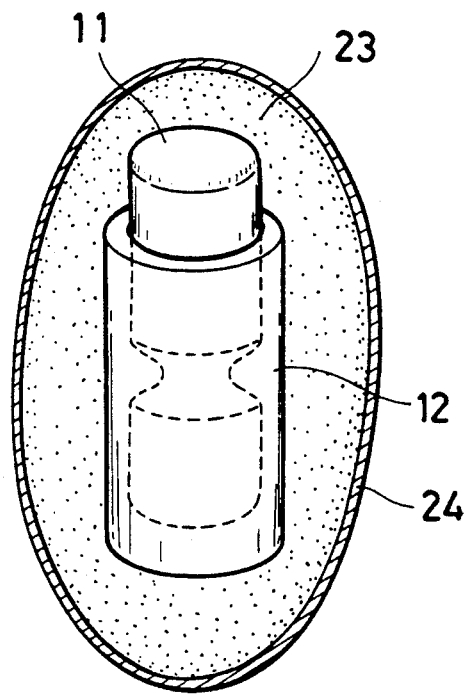
Figure 3:
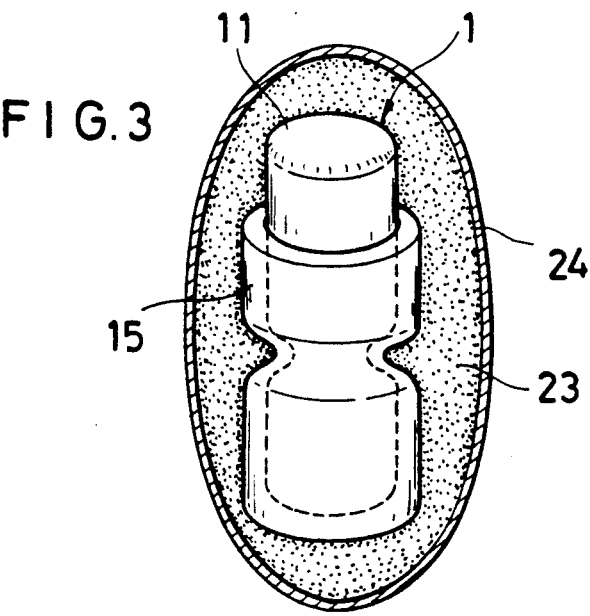

Referring to FIGS. 1 to 3, an assembly of a substrate and a cover is shown in perspective views to illustrate the method for preparing a composite body using the HIP process. The elements involved in this method are a substrate 11, a cover 12 formed of superplastic ceramic material, a surrounding/pressurizing medium 23 in the form of ceramic powder, and an enclosure 24 in the form of a glass envelope for enclosing the foregoing three elements in a stationary manner.

The substrate 11 is preferably formed of a material which can withstand repetitive stresses and has a flexural strength of 200 MPa or higher, sometimes as high as 1500 MPa and a high melting point of 700° C. or higher. Also preferably, the substrate material undergoes little deformation, say, a deformation of less than 10%, during superplastic HIP joining. Preferred examples of the substrate material include metals and ceramics, which should be non-harmful to living bodies in the case of living hard tissue replacements. The metals include elemental metals such as Ti, W, Mo, Au, and Pt and alloys such as Ni-Cr, Ni-Ti, Fe-Cr-Al, Ti-Zr, Fe-Ni-Cr, Ti-Al-V, Co-Cr, Co-Cr-Mo, Ti-Mo, and stainless steel. The useful ceramics include high strength ceramics such as zirconia, SiC, SiN, BN, and $Al_2O_3$.

The cover 12 is of a superplastic ceramic material which is selected from biologically active calcium phosphate base ceramic materials such as apatite and tricalcium phosphate as previously described. More particularly, the cover 12 is formed from a sintered ceramic material having a predetermined grain size. The configuration and dimensions of the cover 12 may be determined in accordance with the configuration and dimensions of the substrate 11.

It is desired that the difference in thermal expansion coefficient between the substrate 11 and the cover 12 be within 50%, preferably within 40%, more preferably within 10%.

The ceramic powder used as the surrounding/pressurizing medium 23 includes zirconia, alumina, BN, SiC, SiN, WC, and partially stabilized zirconia although high temperature ceramics which do not melt at the superplastic forming temperature involved in the HIP process, especially at 700° C. or higher temperatures are preferred. A proper choice should be made of the particle size of the ceramic powder 23 since the cover 12 joined to the substrate by superplastic forming can have a surface roughness corresponding to the selected particle size of the surrounding powder. Therefore, the ceramic powder may have a particle size of about 10 to about 500 $\mu$m. The ceramic powder layer 23 is generally about 0.5 mm to about 50 mm thick.

The glass envelope 24 may be formed of silica glass, boron oxide glass, silicate glass, borosilicate glass, germanate glass, phosphate glass or the like. It is generally about 100 $\mu$m to about 5,000 $\mu$m thick.

These elements are assembled as follows. First, a suitable support material is shaped and finished to form a substrate or support 11 of predetermined configuration and dimensions depending on the intended use. Also a calcium phosphate base ceramic material is sintered by the CIP or HIP process to form a cylindrical cover or sleeve 12. The cover or sleeve 12 generally has a wall thickness of up to 10 mm, preferably 10 $\mu$m to 3 mm. Then the substrate 11 is fitted and received in the cover 12 as shown in FIG. 1. Preferably the substrate 11 is snugly fitted in the cover 12 with the gap therebetween being as small as 0.3 mm or less.

The substrate 11 has substantially the same configuration as the final product. More particularly, the substrate 11 may be provided with grooves, recesses, ridges, or rims on its surface if desired. In the illustrated example, the substrate 11 is a cylinder formed with a circumferential groove at an axial intermediate. The configured substrate 11 may be prepared by sintering, casting, and/or machining.

Also, the cover 12 has substantially the same outer configuration as the final product. However, the cover 12 may take a simple configuration having a smooth outer surface while necessary surface irregularities can be omitted at this point. This leads to efficiency of manufacture because only the substrate 11 need precise shaping and the cover 12 can have a simple configuration. The simple configuration allows the cover to be formed to a uniform wall thickness, resulting in the final coating with a uniform thickness.

Next, the assembly of substrate 11 fitted in cover 12 is covered with ceramic powder 23 and enclosed in the glass envelope 24 as shown in FIG. 2.

The envelope is then loaded in a conventional HIP apparatus which applies heat and pressure to the envelope, creating a strong junction between substrate 11 and cover 12. There results an integral or composite body 1 in which a coat 15 is closely bonded to the substrate 11 as shown in FIG. 3. At the end of HIP forming, the glass envelope 24 is broken and the composite body 1 is taken out.

During the HIP process, the substrate 11 is little deformed and the coat 15 of uniform thickness closely conforms to the outer contour of substrate 11. The isostatic pressing minimizes the chance of poor bond.

The coat 15 on the composite body 1 generally has a thickness of from about 1 $\mu$m to about 10 mm, preferably from 1 $\mu$m to 5 mm, more preferably from 10 $\mu$m to 3 mm. The coat 15 does not peel away even when it is relatively thick as several millimeters.

The coat 15 can be finished to a mirror or rough surface through a proper choice of the particle size of the surrounding ceramic powder 23. For increased surface area and biological activity, the coat should have a rough surface having a surface roughness Rmax of about 10 to about 500 $\mu$m.

The superplastic junction using an HIP process has been described. In the practice of the invention, a hot pressing (HP) process may also be used to establish a junction insofar as the substrate 11 having substantially the same configuration as the final composite body 1 can be combined with a cover 12 of a simple configuration capable of fitting over the substrate.

The HP process involves the steps of engaging the substrate 11 with the cover 12 in place, embedding the assembly in the ceramic powder 23 in a press mold, and forcing a punch thereto. The press mold is preferably formed of the same or similar material as the ceramic powder. Then a bond is established to a degree substantially equal to the HIP process.

The composite body thus obtained may be utilized as parts at least partially embedded in a living body, for example, artificial dental parts such as dental roots and crowns, artificial bones (including general bones, skull, ossiculum auditus, jaw bone, cartilagines ansi, etc.), bone replacements, artificial joints, fracture fixtures, artificial valves, and artificial blood vessels as well as medical equipment, for example, hypodermic implanting equipment such as dialysis shunts, living body embedding equipment such as pacemakers, and other living body indwelling equipment. The composite body is best suited as living hard tissue replacements.

Now, the application of the composite body of the invention to an artificial dental root and crown as a typical living hard tissue replacement is described.

The artificial dental root and crown are preferably of the construction in which a sintered calcium phosphate base ceramic material is joined to the surface of a substrate by superplastic forming.

Figure 4:
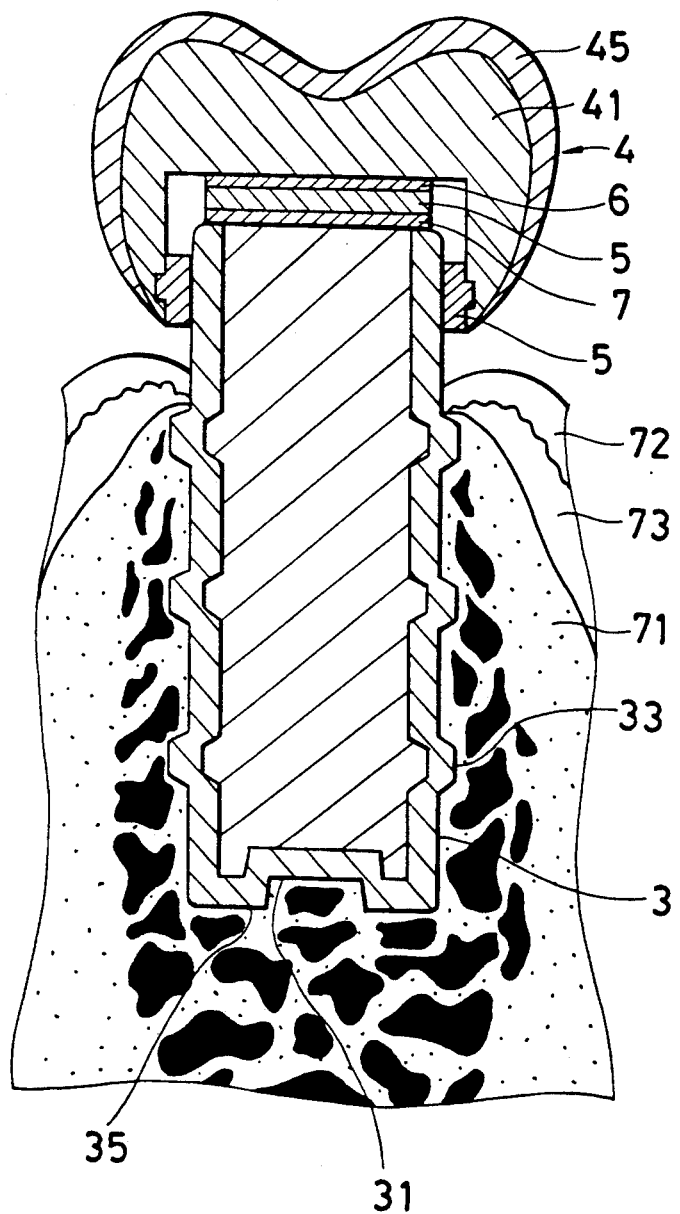
FIG. 4 is a cross-sectional view of a dental root implanted in an alveolar bone, the root having a crown cemented thereto.

FIG. 4 shows an artificial dental root and crown according to one preferred embodiment of the invention. An artificial dental root 3 to which a crown 4 is secured through a damping member 5 by cement layers 6 and 7 is implanted in an alveolar bone 71.

The dental root 3 includes a root substrate 31 and a coat layer 35 bonded to the substrate surface. The root 3 on the outer surface is formed with a plurality of tabs or threads 33. The tabs 33 have an anchoring function and a function of defining gaps between the root 3 and the alveolar bone 71. The root 3 does not directly integrate with the surrounding alveolar bone 71, but a neoblastic bone which will form around the root. The provision of tabs 33 promotes the growth of a new bone, ensuring a firm bond between the root 3 and the alveolar bone 71. The shape of tabs 33 is not critical, and they may be circumferential rings, screw threads or discrete protuberances on the outer surface of the root 3. The tabs 33 are generally 100 $\mu$m to 3 mm in radial height.

The configuration and dimensions of substrate 31 are not critical. The substrate may be configured to the shape and dimensions corresponding to the intended artificial dental root as previously described. It is preferably formed with tabs corresponding to the tabs 33. It is preferably formed from a safe material having high mechanical strength and toughness as previously described, inter alia, titanium, titanium alloy, zirconia, and monocrystalline alumina (sapphire).

The coat layer 35 on the root substrate 31 is formed from a calcium phosphate base ceramic material and joined to the substrate 31 by superplastic forming. The coat layer 35 is initially a hollow cylinder having one closed end and one open end formed from a sintered calcium phosphate base ceramic material and adapted to fit over the substrate 31. The cover cylinder is preferably about 10 $\mu$m to about 10 mm thick. The superplastic forming causes the cover cylinder of calcium phosphate base ceramic material to deform in conformity with the outer contour of substrate 11 and to bond to the substrate 11 without leaving a gap. The coat layer 35 of uniform thickness is joined to the substrate 11 in this way. The coat layer 35 preferably has a thickness of 1 $\mu$m to 5 mm, more preferably from 10 $\mu$m to 2 mm.

The coat layer 35 should be present at least on those surface areas of the artificial dental root 3 which come in contact with a living body, for example, the alveolar bone 71, gingival epithelium 72, and subepithelial connective tissue 73 in FIG. 4.

The artificial dental root 3 of the above-mentioned construction is not particularly limited in shape. A choice may be made of circular, oval, and rectangular column and blade shapes. It is preferred to provide tabs 33 as previously described. In general, the artificial dental root 3 has a maximum diameter of 2 to 20 mm and a height of 3 to 50 mm. It may be configured to any desired dimensions Q in accordance with various standards or to special dimensions if necessary.

Although the artificial dental root 3 shown in FIG. 4 is a one-piece member, the invention is also applicable to two-piece dental roots having a post core and multiple-piece dental roots having three or more components. These roots should have a coat layer of calcium phosphate base ceramic material on at least the surface to be in contact with a living body.

The dental crown 4 includes a coronal substrate 41 and a coat layer 45 bonded to the substrate surface. The coat layer 45 is formed of sintered calcium phosphate base ceramic material and joined to the coronal substrate 41 by superplastic forming. An initial cover which is fitted over the substrate and eventually converted into the coat layer 45 may have any appropriate thickness depending on the desired configuration and thickness of the coat layer.

The configuration and dimensions of coronal substrate 41 are not critical. The coronal substrate 41 may be configured to a columnar or pyramid shape having a recess at its bottom for receiving the root or a combination of such shapes. The top side of the coronal substrate 41 may be flat, but preferably configured to a complex shape conforming to the intended crown. More particularly, the crown configuration largely differs between incisive and molar teeth. Thus, the use of a coronal substrate 41 configured to a shape conforming to a particular incisive or molar tooth leads to ease of forming because the sintered calcium phosphate base ceramic material requires minimal deformation. The material of which the coronal substrate 41 is formed may be selected from the same materials as previously mentioned for the root substrate.

In order that the crown 4 have an aesthetic appearance similar to a natural tooth, biological affinity, and no detrimental influence to the gingival epithelium 72, the coat layer 45 should preferably surround the entire outer surface of the coronal substrate 41. The coat layer 45 generally has a thickness of about 1 $\mu$m to about 5 mm.

The crown 4 illustrated in FIG. 4 is a single component crown although the present structure is applicable to the outer crown component of a two-component crown.

The artificial dental crown 4 is secured to the artificial dental root 3 through the damping members 5 by cement layers 6 and 7 as shown in FIG. 4. The damping members 5 are effective for damping shocks applied to the root during mastication and gnash. Cementing of the crown to the root through the damping members allows the crown to fluctuate like a natural tooth. The damping members 5 are often formed of synthetic rubber to a thickness of about 0.01 to about 4 mm. The cement layers 6 and 7 may be of a conventional dental cement.

The artificial dental root according to the invention is not only useful as an implant embedded in an alveolar bone when combined with the artificial crown as shown in FIG. 4, but also as an intradental implant by inserting the artificial root into a natural tooth.

The artificial dental root combined with the artificial dental crown according to the invention is also useful in full and partial denture sets, and free-standing tooth replacements.

The artificial dental root and crown according to the invention may be independently used in practice. That is, the artificial dental crown and root to be combined with the artificial dental root and crown according to the invention, respectively, need not have a coat layer of calcium phosphate base ceramic material. The artificial dental root and crown according to the invention are effective even when they are combined with conventional artificial dental crown and root.

EXAMPLE

Examples of the present invention are given below by way of illustration and not by way of limitation.

EXAMPLE 1

Dental Root

Hydroxyapatite prepared by a wet process having a Ca/P atom ratio of 1.67 and a specific surface area of 80 m$^2$/g in BET was subjected to unidirectional pressing under a pressure of 50 kg/cm$^2$, and then to cold isostatic pressing (CIP) under a pressure of 2,900 kg/cm$^2$. It was then calcined for two hours at 1,000° C. in air and then HIP sintered for two hours at 1,000° C. and 2,000 atm. in argon gas, obtaining a cylindrical sintered body. This cylindrical sintered body had a diameter of 4 mm, a height of 20 mm, a relative density of 99.9%, and an average grain size of 0.64 $\mu$m.

The sintered body was subjected to forming in an inert gas atmosphere using an artificial dental root-shaped mold of molybdenum base alloy (TZM). The forming conditions included a holding temperature of 1,050° C., a compression rate of 1.0 mm/min., a compression force of 60 MPa, and a deformation of 0.5 in true strain. The forming resulted in an artificial dental root of hydroxyapatite. It was observed at the end of forming that the average grain size was 1.0 $\mu$m and the grains had been distorted and oriented.

EXAMPLE 2

Dental Crown

A sintered body of hydroxyapatite was obtained by the same procedure as in Example 1 except that the body was dimensioned 7 mm by 7 mm by 7 mm. The sintered body was formed by extruding into an artificial dental crown-shaped mold of CaO-TiO$_2$-ZrO$_2$-MgCl$_2$ ceramic material. The forming conditions were the same as in Example 1. It was observed at the end of forming that the average grain size was 1.0 $\mu$m and the grains had been distorted and oriented.

EXAMPLE 3

Dental Root

Hydroxyapatite prepared by a wet process having a Ca/P atom ratio of 1.67 and a specific surface area of 80 m$^2$/g in BET was subjected to unidirectional pressing under a pressure of 50 kg/cm$^2$, and then to cold isostatic pressing (CIP) under a pressure of 2,900 kg/cm$^2$. It was then calcined for two hours at 1,000° C. in air and then HIP sintered for two hours at 1,000° C. and 2,000 atm. in argon gas, obtaining a sintered plate. This sintered plate had dimensions of 25 mm by 20 mm by 4 mm, a relative density of 99.9%, and an average grain size of 0.64 $\mu$m.

The sintered plate was subjected to forming by extruding into a mold using a dental root substrate as the extruder head. The root substrate was a columnar piece of titanium having a diameter of 2 mm and a height of 18 mm. The forming conditions included a holding temperature of 1,000° C., a compression rate of 1.0 mm/min., a compression force of 60 MPa, and a deformation of 0.5 in true strain. The forming resulted in an artificial dental root having a hydroxyapatite coat layer of 2 mm thick joined to the root substrate surface. The bond strength between the substrate and the coat layer was 350 MPa. It was observed that the coat layer had an average grain size of 1.0 $\mu$m and the grains had been distorted and oriented.

EXAMPLE 4

Dental Crown

A sintered plate of hydroxyapatite was obtained by the same procedure as in Example 3 except that the plate was dimensioned 25 mm by 20 mm by 4 mm.

The sintered plate was subjected to forming by extruding into a mold of CaO-TiO$_2$-ZrO$_2$-MgCl$_2$ ceramic material using a dental crown substrate as the extruder head. The coronal substrate had been shaped from yttrium-containing zirconia to a standard molar tooth configuration. The forming conditions were the same as in Example 3. The forming resulted in an artificial dental crown having a hydroxyapatite coat layer of 1 to 2 mm thick joined to the coronal substrate surface. The bond strength between the substrate and the coat layer was 350 MPa. It was observed that the coat layer had an average grain size of 1.0 μm and the grains had been distorted and oriented.

EXAMPLE 5

Dental Root

Hydroxyapatite prepared by a wet process having a Ca/P atom ratio of 1.67 and a specific surface area of 80 $m^2/g$ in BET was subjected to unidirectional pressing under a pressure of 50 $kg/cm^2$, and then to cold isostatic pressing (CIP) under a pressure of 2,900 $kg/cm^2$. It was then calcined for two hours at 1,000° C. in air and then HIP sintered for two hours at 1,000° C. and 2,000 atm. in argon gas, obtaining a sintered hollow cylinder closed at one end, but open at the other end. This sintered cylinder serving as a cover or sleeve had a wall thickness of 2 mm, an average grain size of 0.6 μm, and a coefficient of thermal expansion of $12 \times 10^{-6}$.

A solid columnar piece of titanium with a coefficient of thermal expansion of $8.4 \times 10^{-6}$ serving as a root substrate was fitted in the hollow sintered cylinder as shown in FIG. 1. The titanium piece had a diameter of 2 mm and a height of 18 mm and a plurality of tabs on the outer surface (see FIG. 4). The assembly was covered with zirconia ceramic powder having a high melting point (which does not melt at 700° C. or higher) and an average particle size of 0.3 μm, and further enclosed in a silica glass envelope as shown in FIG. 2. Superplastic forming was effected by an HIP process under the conditions: a temperature of 900° C., a pressure of 60 MPa, and a time of 30 minutes.

At the end of HIP forming, the glass envelope was broken and the zirconia powder was brushed off. There was obtained an artificial dental root having a hydroxyapatite coat layer of 1.9 mm thick joined to the root substrate surface. The bond strength between the substrate and the coat layer was 100 MPa, as represented by the peel strength which was measured by withdrawing the root substrate from the joined root substrate coat assembly secured in a jig. The coat layer had a surface roughness Rmax of 100 μm and a flexural strength of 450 MPa.

EXAMPLE 6

Dental Crown

A sintered hollow cylinder of hydroxyapatite was obtained by the same procedure as in Example 6.

The sintered hollow cylinder serving as a crown cover was fitted over a coronal substrate of titanium. The assembly was subjected to superplastic forming by a HIP process under the same conditions as in Example 5. There was obtained an artificial dental crown whose physical properties were approximately equal to those of the root in Example 5.

Using the same substrate, cover, and ceramic powder as in Examples 5 and 6, the assembly was subjected to superplastic forming by a HP process under approximately the same conditions as in the HIP process. Approximately equivalent results were obtained.

Biological affinity tests were performed on the dental root samples of Examples 1, 3 and 5.

The dental roots were implanted in holes of $3 \times 4 \times 6$ mm formed in the jaw bone of male adult rabbits weighing 2.5 to 2.8 kg. Polished, but non-decalsified specimens were prepared after the lapse of six weeks from the operation. An SEM photomicrograph was taken on the interface between the root and the newly grown bone. It was found in all examples that the newly grown bone completely adhered to the root (implant) and penetrated and filled into pores therein, proving that the roots had high biological affinity.

A high resolution image was taken under a TEM on the interface between the artificial dental root and the matrix bone after 24 weeks. The sequence of bone cells was identical on both the root and matrix bone sides, with little or no distinct boundary observed therebetween.

There has been described a living hard tissue replacement or implant which is prepared from calcium phosphate base ceramic material by superplastic forming. Replacements of desired configuration, surface nature, and dimensional precision can be prepared simply by exchanging a mold used in the forming process. Although the need for tailoring an implant to particular configuration and dimensions corresponding to an individual patient imposed many problems to implants with respect to molding and shaping, the present invention enables the preparation of an implant meeting a particular patient's site by forming the implant in a particular mold conforming to the site. Replacements of complex shape can be readily prepared while their surface nature can be a mirror or rough surface through a proper choice of the mold. Strength is not lost by processing. Particularly when the living hard tissue replacements or implants are formed from calcium fluorophosphate, there are obtained artificial dental roots which are fully resistant against dental caries and acids.

There has also been described a composite body in which a calcium phosphate base ceramic material is firmly joined to a heterogeneous material by superplastic forming. The firm joint can be achieved at relatively low temperatures.

The living hard tissue replacement and composite body need not be profile finished by machining. They are thus free from flaws and defects which cause to create cracks during repetitive use. It is possible to prepare a replacement or composite body having an outer surface with complex irregularities which cannot be reproduced by machining.

In particular, the composite body preparation method using an HIP process allows pressure to be evenly applied to the constituent materials to provide an increased bonding force, avoiding any gaps being left at the interface between the substrate and the coat and preventing exfoliation at the interface during repetitive use.

Since no exfoliation occurs with an increasing thickness of a calcium phosphate base ceramic material layer, the coat layer can have any desired thickness. The coat layer may be either as thin as about 1 μm or as thick as about 10 mm. The coat layer thickness may be selected over the wide range depending on the intended use. In addition, the coat layer can be applied to a uniform thickness without a substantial variation and to a complex configuration with ease. The variation in quality among composite products is minimized.

The composite products can be controlled to any desired surface roughness through a choice of the particle size of ceramic powder to be filled around the calcium phosphate base ceramic material/heterogeneous material assembly during HIP or HP forming.

A composite body can be prepared from a substrate and a cover by shaping only the substrate to a precise configuration, fitting the ceramic cover of a roughly conforming shape over the substrate, and subjecting the assembly to superplastic forming. Steps of shaping, bonding, and surface treatment can be concurrently performed by a single forming step, with the benefits of eliminated need for machining and increased efficiency of working and manufacture. A plurality of composite bodies can be produced at the same time so that a cost reduction is expectable from potential mass production.

The method for preparing a composite body according to the invention ensures that living hard tissue replacements having improved mechanical strength, biological affinity, and formability and well suited as artificial dental roots and crowns are produced at a low cost.

Although some preferred embodiments have been described, many modifications and variations may be made thereto in the light of the above teachings. It is therefore to be understood that within the scope of the appended claims, the invention may be practiced otherwise than as specifically described.

We claim:

1. A living hard tissue replacement prepared by the superplastic forming of a calcium phosphate base ceramic material to a deformation of at least about 0.1 in true strain.

2. A living hard tissue replacement prepared by superplastic forming a calcium phosphate base ceramic material having an average grain size of up to 10 μm to a deformation of at least about 0.1 in true strain.

3. The tissue replacement of claim 1 or 2, wherein the superplastic forming is carried out at a temperature of 500° to 1,600° C.

4. A living hard tissue replacement in the form of a composite body prepared by joining a calcium phosphate base ceramic material and a material of different type of superplastic forming.

5. The tissue replacement of claim 4 wherein said material of different type is a metal or ceramic material.

6. The tissue replacement of claim 4 wherein the joining step includes hot isostatic pressing.

7. The tissue replacement of claim 6 which further includes
shaping said material of different type into a substrate and
joining a cover of said ceramic material to the substrate.

8. The tissue replacement of claim 7 wherein said molding step includes molding the substrate to substantially the same shape as the composite body, and
said joining step includes applying a cover of the superplastic ceramic material to said substrate and effecting hot isostatic pressing on the covered substrate through ceramic powder.

9. The tissue replacement of claim 1 which further includes
shaping said material of different type into a substrate having substantially the same shape as the composite body,
covering said substrate with the superplastic ceramic material, and
effecting hot pressing, thereby joining said superplastic ceramic material to the substrate.

10. The tissue replacement of claim 9 wherein said substrate covered with said superplastic ceramic material is hot pressed through ceramic powder.

11. A living hard tissue replacement comprising:
a calcium phosphate base ceramic material; and
a substrate formed of a material different than said calcium phosphate base ceramic material;
wherein said substrate defines a predetermined configuration based on intended use and said calcium phosphate base ceramic material is joined to said substrate by superplastic forming so as to form a cover on said substrate.

12. The living hard tissue replacement of claim 11 in the form of an artificial dental root, artificial dental crown or artificial bone.

13. The living hard tissue replacement of claim 11, further comprising:
a ceramic powder surrounding said substrate covered by said calcium phosphate base ceramic material; and
a glass envelope enclosing said substrate covered by said calcium phosphate base ceramic material and surrounded by said ceramic powder;
wherein heat and pressure are applied to said enclosed substrate and calcium phosphate base ceramic material so as to bond said substrate and said calcium phosphate base ceramic material.

14. A living hard tissue replacement in the form of a composite body prepared by forming a calcium phosphate organic material having an average grain size of up to 10 μm and joining a calcium phosphate base ceramic material and a material of different type of superplastic forming;
wherein said material of different type is molded into substantially the same shape as the composite body and said calcium phosphate base ceramic material is disposed on said material of different type so as to cover said material of different type.

* * * * *

UNITED STATES PATENT AND TRADEMARK OFFICE
CERTIFICATE OF CORRECTION

PATENT NO. : 5,123,844
DATED : June 23, 1992
INVENTOR(S) : Fumihiro Wakai et al.

It is certified that error appears in the above-identified patent and that said Letters Patent is hereby corrected as shown below:

On the title page:
   The Assignee is incorrect. [73], should be, --Agency of Industrial Science and Technology, Ministry of International Trade and Industry; TDK Corporation, both of Tokyo, Japan--.

Signed and Sealed this

Ninth Day of November, 1993

Attest:

BRUCE LEHMAN

Attesting Officer

Commissioner of Patents and Trademarks